(12) United States Patent
Fritz et al.

(10) Patent No.: US 7,723,557 B2
(45) Date of Patent: May 25, 2010

(54) METHOD FOR THE PREPARATION OF LINEAR ALPHA-OLEFINS AND REACTOR SYSTEM THEREFORE WITH IMPROVED DISPOSAL OF HIGH MOLECULAR WEIGHT OLIGOMERS

(75) Inventors: Peter Fritz, Unterhaching (DE); Heinz Bölt, Wolfratshausen (DE); Stefan Glanz, Neubiberg (DE); Richard Schneider, Uffing (DE); Talal Ali, Riyadh (SA); Sultan Al-Otaibi, Riyadh (SA); Fuad Mosa, Riyadh (SA)

(73) Assignees: Saudi Basic Industries Corporation, Riyadh (SA); Linde AG, Munich (DE)

( * ) Notice: Subject to any disclaimer, the term of this patent is extended or adjusted under 35 U.S.C. 154(b) by 0 days.

(21) Appl. No.: 11/989,831

(22) PCT Filed: Jun. 13, 2006

(86) PCT No.: PCT/EP2006/005641

§ 371 (c)(1),
(2), (4) Date: Jan. 16, 2009

(87) PCT Pub. No.: WO2007/016992

PCT Pub. Date: Feb. 15, 2007

(65) Prior Publication Data

US 2009/0221769 A1    Sep. 3, 2009

(30) Foreign Application Priority Data

Jul. 29, 2005   (EP)   ................... 05016524

(51) Int. Cl.
*C07C 7/00* (2006.01)
(52) U.S. Cl. ...................................... 585/867; 585/901
(58) Field of Classification Search ................ 585/867, 585/901
See application file for complete search history.

(56) References Cited

U.S. PATENT DOCUMENTS

| 4,547,612 A | * | 10/1985 | Tabak ........................ 585/533 |
| 5,496,783 A | * | 3/1996 | Chauvin et al. ............. 502/125 |
| 5,523,508 A | * | 6/1996 | Krawczyk et al. ........... 585/523 |
| 5,817,905 A | | 10/1998 | Commereuc |
| 6,221,986 B1 | | 4/2001 | Commereuc |

* cited by examiner

*Primary Examiner*—David Wu
*Assistant Examiner*—Elizabeth Eng
(74) *Attorney, Agent, or Firm*—Kramer Levin Naftalis & Frankel LLP

(57) ABSTRACT

The present invention relates to a method for processing high molecular weight oligomer waste products formed during the production of linear alpha-olefins by oligomerization of ethylene in a reactor in the presence of a solvent and a catalyst, characterized in that the high molecular weight oligomers are separated in a separation unit from a product stream of the reactor comprising the solvent, the catalyst, linear alpha-olefins and high molecular weight oligomers having a solidification temperature in the range of about 60-100° C., then diluted with a dilution medium and heated to about 130° C. to about 200° C., the diluted high molecular weight oligomers are then transferred to a disposal device, wherein at least some of the dilution medium may be recovered and recycled for addition to the dilution medium.

9 Claims, 1 Drawing Sheet

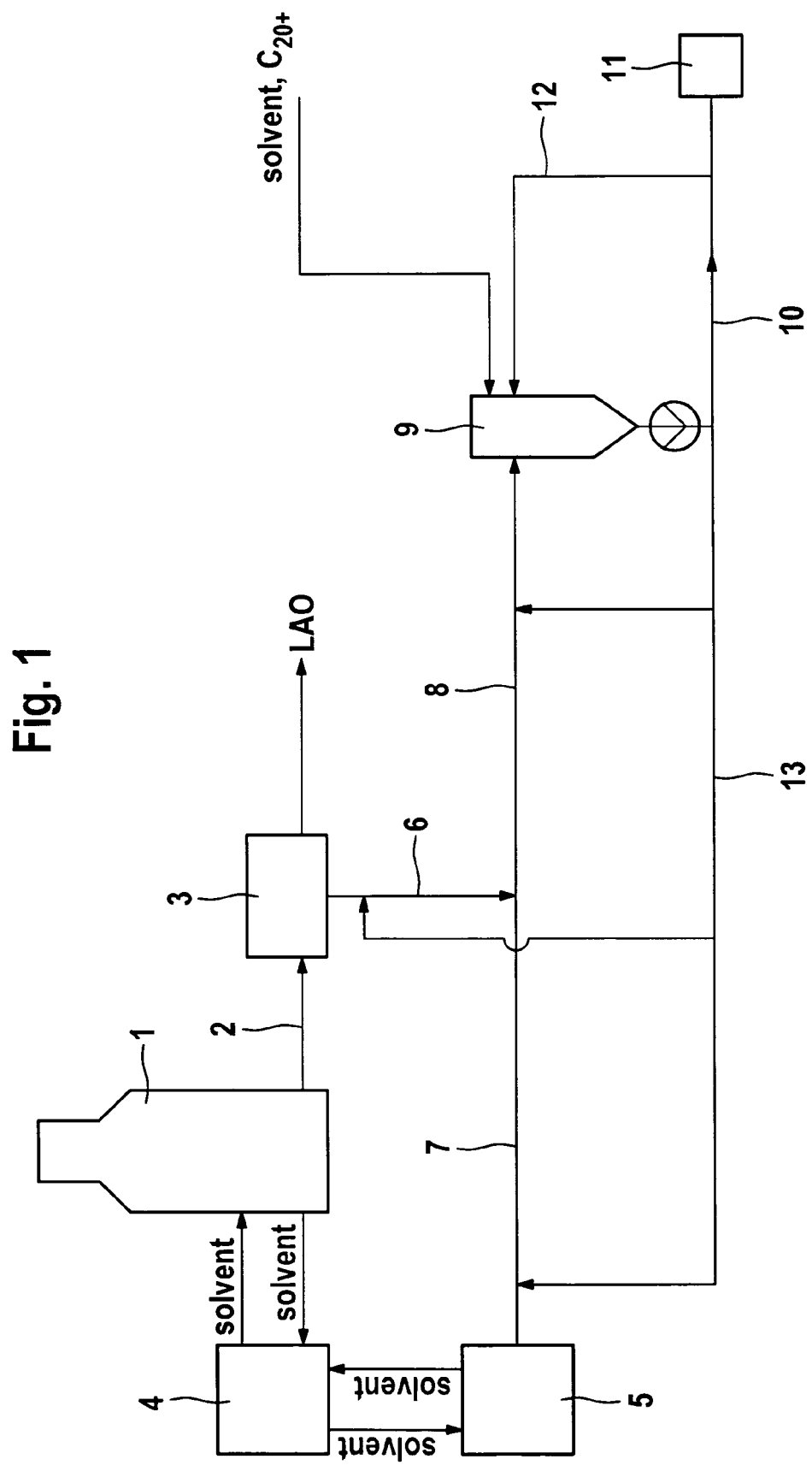

METHOD FOR THE PREPARATION OF LINEAR ALPHA-OLEFINS AND REACTOR SYSTEM THEREFORE WITH IMPROVED DISPOSAL OF HIGH MOLECULAR WEIGHT OLIGOMERS

The present invention relates to a method for the preparation of linear alpha-olefins by oligomerization of ethylene in a reactor in the presence of a solvent and a catalyst.

Oligomerization methods for preparing linear alpha-olefins are widely known in the art. This method is usually carried out in the presence of a catalyst preferably comprising a zirconium component, such as zirconium tetraisobutyrate, and an aluminum component as activator, such as ethyl aluminum sesquichloride.

One problem associated with such oligomerization methods is that not only liquid linear alpha-olefins with desired chain length, e.g. $C_4$-$C_{18}$, are prepared, but also high molecular weight oligomers which are solid at reaction temperature of about 60-100° C. and have to be removed from the plant to avoid plugging. Such high molecular weight oligomers may be separated from the desired alpha-olefin products. A further problem is the disposal of high molecular weight oligomers from the plant, as the amount of high molecular weight oligomers produced is low (some kg/h) and it is often required to transfer the high molecular weight oligomers over a large distance to a disposal device. In the piping connecting the reactor unit and the disposal device, such as an incinerator, as well as in any equipment and piping which are in contact with high molecular weight oligomers containing streams, plugging may occur. This plugging may also occur due to the low flow rates in the reactor system.

In some cases, the distance between the oligomerization reactor and the disposal device is large, for example, about 1 to about 2 kilometers. Thus, small amounts of high molecular weight oligomers (in the range of some kilogram/h) are difficult to transfer to the disposal device due to long residence time, and this often results in plugging of equipment and piping.

It is therefore an object of the present invention to provide a method for the preparation of linear alpha-olefins which overcomes the disadvantages of the prior art, especially a method shall be provided which avoids plugging of equipment and piping which are in contact with high molecular weight oligomers containing streams.

This object is achieved in that a discharge stream of the reactor comprising the solvent, catalyst, linear alpha-olefins and substantially high molecular weight oligomers, the high molecular weight oligomers are separated, then diluted with a dilution medium and heated to about 130° C. to about 200° C., the diluted high molecular weight oligomers being then transferred to a disposal device, wherein recycles for loop operation are established, and flow rates of the loop streams are from about 1 to about 50 m³/h.

Preferably, the high molecular weight oligomers are separated in a separation unit, preferably a filter unit or a distillation unit.

Preferably, the temperature in the reactor is from about 60 to about 100° C.

The solvent may be toluene and the dilution medium may be toluene and/or a liquid fraction of the oligomerization product comprising oligomers having more than 18 carbon atoms.

In one preferred embodiment, the dilution medium comprises the bottom product of a purification apparatus, preferably a distillation column, for the solvent.

The dilution medium may comprise high molecular weight oligomers.

The method is further characterized in that the dilution medium with dissolved high molecular weight oligomers is recycled in a loop to increase flow rates from kg/h to m³/h with corresponding stream velocities to avoid plugging of lines.

Preferably, the disposal device is an incinerator.

It is also proposed that the high molecular weight oligomers containing streams are agitated.

Additionally, the dilution ratio of the dilution medium: high molecular weight oligomer may be about 5:1 to about 15:1, preferably about 10:1.

Finally, according to the invention a reactor system for preparing linear alpha-olefins is provided, especially by an inventive method, comprising a reactor, a separation unit for separating high molecular weight oligomers, recycle loops, and a transfer line to a disposal device.

Surprisingly, it was found that especially due to the dilution of the high molecular weight oligomers with dilution medium and heating thereof to higher temperatures, plugging of equipment and piping which are in contact with high molecular weight oligomers containing streams can be substantially avoided. Further, no handling of high viscous/solid materials is necessary. Due to the low concentration of the high molecular weight oligomers in the dilution medium, the heat tracing requirements in the inventive method are substantially reduced. Further, the plant availability and reliability in which the oligomerization method is conducted are improved.

It is obvious that the inventive method is not necessarily restricted to the oligomerization of ethylene to obtain linear alpha-olefins, but may be utilized in all technologies handling high molecular weight oligomers.

Additional features and advantages of the inventive method are now illustrated in detail with reference to the accompanying drawing wherein FIG. 1 shows a schematic illustration of the inventive method for the preparation of linear alpha-olefins.

In FIG. 1 a reactor 1 for the oligomerization of ethylene to prepare linear alpha-olefins is provided. In the reactor 1 ethylene is oligomerized in the presence of a solvent and a catalyst, preferably at a temperature of about 60-100° C. After oligomerization (the reactor is preferably operated continuously), a discharge stream is removed from the reactor via a discharge line 2. The discharge stream comprises the solvent, catalyst, liquid linear alpha-olefins and high molecular weight oligomers. The term "high molecular weight oligomers" is meant to comprise oligomers having such a high molecular weight that they are substantially solid at reaction temperature. Additionally, further discharge and feed lines are connected to the reactor, but are omitted for purposes of clarity. The discharge stream may be transferred via the discharge line 2 to a separation unit 3, also held at a temperature of about 60-100° C., wherein solid high molecular weight oligomers are separated from the liquid discharge stream. The separation unit may be a filter or any other means suitable and known for someone skilled in the art. Such a separation unit is not absolutely necessary, for example, if no high molecular weight oligomers being solid at reaction temperature are present. The discharge stream containing the substantial amount of solvent and liquid linear alpha-olefins may be processed as is known for someone skilled in the art, for example by distillation of the respective linear alpha-olefins.

The solvent utilized for the oligomerization process is preferably toluene. Toluene is provided to and removed from the reactor by a reactor flushing system 4. The reactor flushing system 4 is further connected to a solvent purification apparatus 5, preferably a distillation equipment. In the solvent purification apparatus 5, the solvent may be purified and purified solvent may be reintroduced into the reactor 1. Impurities which may be incorporated in the solvent may be also high molecular weight oligomers which are collected in the bottoms product of the solvent purification apparatus 5. The bottom product may be used as dilution medium.

Separated high molecular weight oligomers are passed via line 6. Additionally, the bottom product comprising also high molecular weight oligomers is removed from the solvent purification apparatus 5 via line 7. Lines 6 and 7 are combined. The combined streams are then heated to a temperature of about 130° C. to about 200° C. so that the high molecular weight oligomers may be diluted or melted (as polyethylene being a major component of the high molecular weight oligomers has a melting point of about 130° C.). Preferably, the weight ratio of high molecular weight oligomers and dilution medium is from about 1:5 to about 1:15, preferably 1:10. In a preferred embodiment, the high molecular weight oligomers containing streams are also agitated. The combined streams may be then transferred via line 8 to a tank 9 where the combined streams may be additionally diluted with further dilution medium. Also, fractions of the linear alpha-olefins having more than 18 carbon atoms may be added at this stage, or even earlier or later. As it is still difficult to find economically attractive applications for the fractions of $C_{20+}$ these fractions may be preferably utilized to dilute the high molecular weight oligomers for disposal. From the tank 9 the diluted high molecular weight oligomers may be then transferred via line 10 to a disposal device, preferably an incinerator 11. From line 10 the diluted high molecular weight oligomers may be also recycled via recycle line 12 into tank 9. The effluent of tank 9 may be also recycled via recycle line 13 to lines 6 and 7.

Utilizing the inventive method, high molecular weight oligomers containing streams are diluted with an appropriate dilution medium, kept at elevated temperature and, optionally, agitated. In the inventive method, stream velocities in the equipment and piping may be kept high by establishing of larger pump flow rates which are in the range of about 1 to about 50 m³/h. Due to the high stream velocities any plugging of equipment and piping may be avoided. Additionally, the viscosity and pressure drop of the piping system can be adjusted by the dilution rate of the high molecular weight oligomers in the dilution medium. Thus, the small amounts of high molecular weight oligomers (in the range of some kg/h) obtained in the inventive method may be easily disposed by dilution and heating with prevention of plugging.

The features disclosed in the foregoing description, in the drawing or in the claims may, both separately and in any combination thereof, be material for realizing the invention in diverse forms thereof.

The invention claimed is:

1. A method for processing high molecular weight oligomers having a solidification temperature between about 60°C.-100°C. which are formed during the production of linear alpha-olefins by oligomerization of ethylene in a reactor in the presence of a solvent and a catalyst, which method avoids the plugging of process lines carrying said high molecular weight oligomers, characterized in that the high molecular weight oligomers are separated from a product stream of the reactor comprising the solvent, the catalyst, linear alpha-olefins and high molecular weight oligomers, and then diluted in a dilution unit with a dilution medium and heated to about 130°C. to about 200°C., the diluted high molecular weight oligomers are then transferred to a disposal device, wherein said dilution medium is recovered and recycled to the dilution unit.

2. The method according to claim 1, wherein the high molecular weight oligomers are separated in a filter unit or a distillation unit.

3. The method according to claim 1, wherein the temperature in the reactor is from about 60°C. to about 100°C.

4. The method according to claim 3, wherein the solvent is toluene.

5. The method according to claim 1, wherein the dilution medium is toluene and/or a liquid fraction of the oligomerization product comprising oligomers having more than 18 carbon atoms.

6. The method according to claim 4, wherein the reactor has a reactor flushing system which uses the solvent to flush the reactor thereby producing a reactor flush stream and the reactor flushing system has a solvent purification apparatus which separates the solvent from higher molecular weight oligomers in the reactor flush stream, thereby producing a reactor flush higher molecular weight oligomers stream, and wherein said reactor flush higher molecular oligomers stream is added to said dilution medium.

7. The method according to claim 6, wherein the high molecular weight oligomers containing streams are agitated.

8. The method according to claim 1, wherein the dilution mediums and the high molecular weight oligomer are combined to a dilution ratio of about 5:1 to about 15:1.

9. The method according to claim 1, wherein the dilution medium and the high molecular weight oligomer are combined to a dilution ratio of about 10:1.

\* \* \* \* \*